United States Patent [19]
Murata et al.

[11] Patent Number: 4,837,366
[45] Date of Patent: Jun. 6, 1989

[54] PREPARATION OF POLYFLUOROALDEHYDES AND POLYFLUOROACETALS

[75] Inventors: Katsuyoshi Murata, Kamifukuoka; Toru Nakazora, Iruma; Takashi Isago, Kamifukuoka, all of Japan

[73] Assignee: Central Glass Company, Limited, Ube, Japan

[21] Appl. No.: 92,680

[22] Filed: Sep. 3, 1987

[30] Foreign Application Priority Data

Sep. 5, 1986 [JP] Japan ................................ 61-208051
Jul. 17, 1987 [JP] Japan ................................ 62-177218

[51] Int. Cl.$^4$ ........................ C07C 45/00; C07C 47/14
[52] U.S. Cl. ..................................... 568/490; 568/491
[58] Field of Search ......................... 568/490, 491, 475

[56] References Cited

U.S. PATENT DOCUMENTS

| | | | |
|---|---|---|---|
| 2,883,429 | 4/1959 | Neville | 568/490 |
| 3,086,994 | 4/1963 | Smidt et al. | 568/491 |
| 3,544,599 | 12/1970 | Sze et al. | |
| 3,833,659 | 9/1974 | Schmerling et al. | 568/491 |
| 4,709,098 | 11/1987 | Dolfini et al. | 568/491 |

FOREIGN PATENT DOCUMENTS 0161340 12/1981 Japan ................................... 568/490

OTHER PUBLICATIONS

"Trifluoropropyne. II, The Triple Bond and the Acetylenic Hydrogen", by Albert Henne et al., J. Am. Chem. Soc., vol. 74, (1952), pp. 650–652.

"The Preparation of Trifluorinated Aldehydes", by Henne et al., J. Am. Chem. Soc., vol. 72, pp. 3370–3371 (1950).

Smidt et al., Katalytische Umsetzungen von Olefinen an Platinmetall-Verbindvngen, *Angew. Chem.*, vol. 71, No. 5, pp. 176–182 (1959).

Smidt et al., Reaktionen Von Palladiumchlorid mit Olefinischen C=C-Doppelbindungen, *Angew. Chem.*, vol. 71, No. 5, p. 626, (1959).

Golding et al., 3,3,3-Trifluoropropan-1-ol and 3,3,3-Trifluoropropanal, *Journal of Fluorine Chemistry*, vol. 30, pp. 153–158 (1985).

*Primary Examiner*—Werren B. Lone
*Attorney, Agent, or Firm*—Fleit, Jacobson, Cohn & Price

[57] ABSTRACT

A group of polyfluoroaldehydes represented by 3,3,3-trifluoropropanal can be formed with very good selectivity by reacting polyfluoroalkenes represented by 3,3,3-trifluoropropene with water in the presence of a source of divalent palladium. A group of polyfluoroacetals represented by 1,1-dialkoxy-3,3,3-trifluoropropane can be formed with very good selectivity by reacting the same polyfluoroalkenes with an alcohol in the presence of a source of divalent palladium.

13 Claims, No Drawings

PREPARATION OF POLYFLUOROALDEHYDES AND POLYFLUOROACETALS

BACKGROUND OF THE INVENTION

This invention relates to a method of preparing a polyfluoroaldehyde or a polyfluoroacetal from a polyfluoroalkene. A representative of polyfluoroaldehydes that can be prepared by this method is 3,3,3-trifluoropropanal which is of use as the material of intermediates of some medicines and agricultural chemicals. 1,1-Dialkoxy-3,3,3-trifluoropropane is a representative of polyfluoroacetals which can be prepared by this method and can be converted into polyfluoroalkylcarboxylic acids useful as lubricants, surface treating agents and intermediates of some medicines and agricultural chemicals.

It is known that 3,3,3-trifluoropropanal $CF_3CH_2CHO$ is obtained by oxidation of 3,3,3-trifluoropropanol $CF_3CH_2CH_2OH$ with sodium dichromate (J. Am. Chem. Soc., 72, 3370(1950)) or by catalytic hydration of trifluoropropyne $CF_3C{\equiv}CH$ (J. Am. Chem. Soc., 74, 650(1952)). However, neither of these methods is deemed industrially practicable because of difficulty in acquiring the starting material and insufficient yield of the desired aldehyde.

As to preparation of 1,1-dialkoxy-3,3,3-trifluoropropane $CF_3CH_2CH(OR)_2$, U.S. Pat. No. 2,883,429 shows reacting a corresponding trifluoroalkenyl ether with an alcohol in the presence of a base. However, the starting material of this method is very expensive and difficult to acquire as an industrial material since it has to be synthesized by complicated multi-stage reactions.

SUMMARY OF THE INVENTION

It is an object of the present invention to provide a method of preparing a group of polyfluoroaldehydes represented by 3,3,3-trifluoropropanal and a group of polyfluoroacetals represented by 1,1-dialkoxy-3,3,3-trifluoropropane by using a relatively inexpensive and industrially easily available compound as the starting material.

According to the invention, there is provided a method of preparing a polyfluorinated organic compound represented by the general formula (1),

$$Rf(CH_2)_nCH_2CH{=}X \quad (1)$$

wherein Rf represents a perfluoroalkyl group having not more than 12 carbon atoms, n is an integer from 0 to 3, and X represents an oxygen atom or two —OR groups wherein R represents an alkyl or alkylene group having not more than 12 carbon atoms, the method being characterized in that a polyfluoroalkene represented by the general formula (2) is reacted with a compound represented by the general formula (3) in the presence of a source of divalent palladium:

$$Rf(CH_2)_nCH{=}CH_2 \quad (2)$$

wherein Rf and n are as defined above with respect to the general formula (1),

$$R'(OH)_m \quad (3)$$

wherein R' represents a hydrogen atom or an alkyl or alkylene group having not more than 12 carbon atoms, and m is 1 or 2.

In this invention a polyfluoroalkene such as, for example, 3,3,3-trifluoropropene is always used as the starting material whether the desired product is a polyfluoroaldehyde or a polyfluoroacetal, and the polyfluoroalkene is reacted with water in the case of preparing a polyfluoroaldehyde and with an alcohol in the case of preparing a polyfluoroacetal. In either case, the polyfluoroalkene is converted very selectively and almost exclusively into a corresponding polyfluoroaldehyde or polyfluoroacetal by carrying out the reaction in the presence of a source of divalent palladium such as a palladium salt. The starting material employed in this invention is relatively inexpensive and easy to acquire as an industrial material. The reaction proceeds under mild conditions, and the yield of the desired aldehyde or acetal is sufficiently high.

A polyfluoroacetal obtained by this method can easily be converted into a corresponding polyfluoroaldehyde by hydrolysis. Even when a polyfluoroaldehyde is wanted as the final product, it will be rather favorable to first prepare a corresponding polyfluoroacetal and hydrolyze it into the aldehyde at an appropriate time since polyfluoroacetals are better in storage stability than polyfluoroaldehydes. In preparing a polyfluoroacetal by this method, if desired it is possible to use water formed by the reaction for hydrolyzing a portion of the formed polyfluoroacetal into a polyfluoroaldehyde or, in other words, to obtain a mixuture of a polyfluoroacetal and a polyfluoroaldehyde by reacting an excess of a polyfluoroalkene over the stoichiometric quantity with the alcohol.

DESCRIPTION OF THE PREFERRED EMBODIMENTS

An industrially important example of polyfluoroalkenes represented by the general formula (2) is 3,3,3-trifluoropropene. The following equation (i) represents the reaction of this compound with water in the presence of a palladium salt, and the equation (ii) the reaction of the same compound with an alcohol in the presence of a palladium salt.

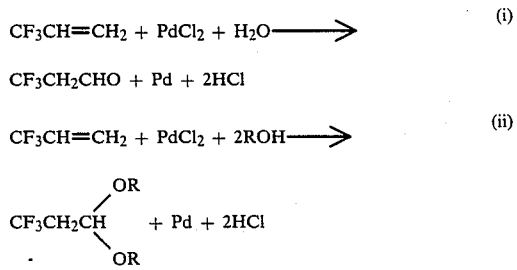

These reactions may be regarded as reactions of the Wacker type. In usual Wacker type reactions of aliphatic compounds, the carbon atom at the 2-position is oxidized. However, in the reactions according to the invention, only the carbon atom at the 1-position is selectively oxidized.

The equations (i) and (ii) represent stoichiometrical reactions. When it is desired that the palladium salt act catalytically, the desire can be met by carrying out each reaction in the presence of an oxidizer for oxidizing metallic Pd isolated by the reaction to divalent Pd and oxygen ($O_2$) for oxidizing the reduced portion of the oxidizer.

Besides 3,3,3-trifluoropropene, important examples of the starting polyfluoroalkene are 3,3,4,4,4-pentafluorobutene and 3,3,4,4,5,5,5-heptafluoropentene.

The alcohol used for preparing a polyfluoroacetal is one having not more than 12 carbon atoms and can be selected from monohydric alcohols and diols represented by ethylene glycol and propanediol.

As the source of divalent palladium it is usual to use a palladium salt such as palladium chloride, palladium sulfate, palladium nitrate or palladium acetate. Also it is possible to use metallic palladium together with an oxidizer to keep palladium in its divalent state in the reaction system. In either case, as an oxidizer it is suitable to use a copper salt such as cuprous or cupric chloride or copper acetate, an iron salt such as ferrous or ferric chloride, hetero-polyphosphoric acid or p-benzoquinone, and it is best to use a copper salt with consideration of performing the reaction in a continuous manner.

In the case of preparing a polyfluoroaldehyde, water as the reactant serves also as a liquid medium for the reaction. However, the polyfluoroalkene as the starting material is low in solubility in water. Therefore, for enhancement of the rate of reaction it is favorable to carry out the reaction in a mixture of water and an organic solvent in which the polyfluoroalkene is soluble. Examples of suitable organic solvents are acetic acid, 1,4-dioxane, N,N-dimethylformamide, dimethyl sulioxide, alcohols such as methanol, ethanol and propanol, and sulfolane derivatives represented by 3-methylsulfolane, and it is best to use acetic acid, 1,4-dioxane or 3-methylsulfolane. Water and a selected organic solvent are mixed such that water amounts to 0.1 to 80 vol %, and preferably 1 to 50 vol %, of the mixture. Since the polyfluoroaldehyde formed by the reaction is not very stable under alkaline conditions it is preferable to render the mixed liquid medium neutral or slightly acidic. In the case of preparing a polyfluoroacetal, it is not necessary to use a liquid medium besides the alcohol as the reactant. However, it is possible to enhance the rate of reaction and suppress formation of unwanted by-products by additionally using an organic solvent. Examples of suitable organic solvents are as named above in regard to the preparation of a polyfluoroaldehyde. Especially it is favorable to use acetic acid, 1,4-dioxane or 3-methylsulfolane.

The reactions according to the invention produce a very small quantity of fluorine. Therefore, it is preferable to add a fluorine removing agent, such as aluminum hydroxide, to the reaction system to thereby prevent lowering of the catalytic activity of palladium and protect the reaction apparatus against corrosion.

In the present invention the reaction temperature is not strictly limited. From a practical point of view a suitable range of the reaction temperature is from room temperature to about 150° C. For enhancement of the rate of reaction it is favorable to carry out the reaction at a relatively high temperature. However, when the reaction temperature is higher than 90° C., undesirable side reactions are liable to take place as a cause of lowering of selectivity to the desired polyfluoroaldehyde or polyfluoroacetal. Accordingly the most suitable range of the reaction temperature is from about 50° C. to 90° C. The reactions according to the invention can be carried out under normal pressure or under elevated pressure, and some pressurization is preferable for enhancement of the rate of reaction.

The invention is further illustrated by the following nonlimiting examples. Examples 1 to 8 relate to preparation of a trifluoroaldehyde, and Examples 9–17 to preparation of trifluoroacetals.

EXAMPLE 1

In a glass autoclave, a mixture of 100 g of water, 150 g of acetic acid, 2.0 g (0.0113 mol) of $PdCl_2$, 3.85 g (0.0226 mol) of $CuCl_2.2H_2O$ and 3.0 g of $Al(OH)_3$ was kept heated at 75° C. Stirring the mixture, 3,3,3-trifluoropropene and oxygen gas in the proportion of 2 to 1 by mol were continuously introduced into the autoclave so as to keep the total gas pressure in the autoclave at 7 kg/cm². This operation was continued for 24 hr, and the resultant mixture was discharged from the autoclave and subjected to distillation.

As the product of the above process 105 g (0.938 mol) of 3,3,3-trifluoropropanal was obtained. In this process, a mean yield of 3,3,3-trifluoropropanal per unit weight of palladium chloride was 2.19 g/g.hr, and in the reaction selectivity to 3,3,3-trifluoropropanal was 97.5%.

EXAMPLE 2

The process of Example 1 was repeated except that aluminum hydroxide was omitted from the initial mixture. In this case 75 g (0.67 mol) of 3,3,3-trifluoropropanal was obtained, and so a mean yield per unit weight of palladium chloride was 1.56 g/g.hr. In the reaction selectivity to 3,3,3-trifluoropropanal was 96.8%.

EXAMPLES 3–5

In these examples the process of Example 1 was modified only in that 1.0 g of 35% hydrochloric acid was added to the water (100 g) and that a different organic solvent was used in place of acetic acid.

In Example 3, 150 g of N,N-dimethylformamide was used, and 24 g (0.21 mol) of 3,3,3-trifluoropropanal was obtained at a mean yield (per unit weight of palladium chloride) of 0.50 g/g.hr. Selectivity to 3,3,3-trifluoropropanal was 95.2%.

In Example 4, 150 g of 1,4-dioxane was used, and 110 g (0.982 mol) of 3,3,3-trifluoropropanal was obtained at a mean yield of 2.29 g/g.hr. Selectivity to 3,3,3-trifluoropropanal was 97.0%.

In Example 5, 150 g of 3-methylsulfolane was used, and 65 g (0.58 mol) of 3,3,3-trifluoropropanal was obtained at a mean yield of 1.35 g/g.hr. Selectivity to 3,3,3-trifluoropropanal was 97.1%.

EXAMPLE 6

The process of Example 1 was modified only in that the quantity of acetic acid was decreased to 100 g and that 2.5 g (0.0113 mol) of palladium acetate was used in place of palladium chloride. As the result 103 g (0.920 mol) of 3,3,3-trifluoropropanal was obtained at a mean yield (per unit weight of palladium acetate) of 1.72 g/g.hr. Selectivity to 3,3,3-trifluoropropanal was 97.1%.

EXAMPLE 7

The process of Example 1 was modified only in that 250 g of 0.1N aqueous soluation of hydrochloric acid was used in place of water and that no organic solvent was used. As the result 11 g (0.098 mol) of 3,3,3-trifluoropropanal was obtained at a mean yield (per unit weight of palladium chloride) of 0.23 g/g.hr. Selectivity to 3,3,3-trifluoropropanal was 95.9%.

EXAMPLE 8

The process of Example 1 was modified in that 24.4 g (0.226 mol) of p-benzoquinone was used as an oxidizer in place of cupric chloride, that 3,3,3-trifluoropropene alone was introduced into the autoclave without using oxygen gas so as to keep the gas pressure in the autoclave at 5 kg/cm$^2$ and that the reaction was carried out for only 3 hr. In this case 10 g (0.089 mol) of 3,3,3-trifluoropropanal was obtained at a mean yield of 1.67 g/g.hr. Selectivity to 3,3,3-trifluoropropanal was 96.3%.

EXAMPLE 9

In a glass autoclave, a mixture of 250 g of methanol, 2.0 g (0.0113 mol) of PdCl$_2$, 3.85 g (0.0226 mol) of CuCl$_2$.2H$_2$O and 3.0 g of Al(OH)$_3$ was kept heated at 60° C. Stirring the mixture, 3,3,3-trifluoropropene and oxygen gas in the proportion of 2 to 1 by mol were continuously introduced into the autoclave so as to keep the total gas pressure in the autoclave at 8 kg/cm$^2$. This operation was continued for 6 hr, and the resultant mixture was discharged from the autoclave and subjected to distillation.

As the result 95.4 g (0.604 mol) of 1,1-dimethoxy-3,3,3-trifluoropropane was obtained. In the reaction selectivity to this polyfluoroacetal was 93.7%, and the remaining part of the reaction product was 3,3,3-trifluoropropanal.

Analytic data of obtained 1,1-dimethoxy-3,3,3-trifluoropropane were as follows.

Boiling point: 97.2° C. at 760 mmHg.

$^1$H-NMR (acetone -d$_6$): δ 2.43 (q, d, $J_{F-H}$=10.5 Hz, $J_{H-H}$=6 Hz, CH$_2$), 3.33 (s, CH$_3$O), 4.66 (t, CH).

$^{19}$F-NMR (acetone -d$_6$): δ (standard: CFCl$_3$) 63.3 (t, CF$_3$).

EXAMPLE 10

The process of Example 9 was repeated except that the quantity of methanol was decreased to 125 g (3.91 mol) and that 125 g of 1,4-dioxane was additionally used. In this case 115.6 g (0.732 mol) of 1,1-dimethoxy-3,3,3-trifluoropropane was obtained. In the reaction selectivity to this compound was 98.6%, and the remaining part of the product was 3,3,3-trifluoropropanal.

EXAMPLES 11–13

In these examples the process of Example 10 was modified only in that a different organic solvent was used in place of 1,4-dioxane.

In Example 11, 125 g of N,N-dimethylformamide was used, and 111.4 g (0.705 mol) of 1,1-dimethoxy-3,3,3-trifluoropropane was obtained. Selectivity to this polyfluoroacetal was 97.2%.

In Example 12, 125 g of 3-methylsulfolane was used, and 107.9 g (0.683 mol) of the same polyfluoroacetal was obtained. Selectivity to this acetal was 96.6%.

In Example 13, 125 g of acetic acid was used, and 116.3 g (0.736 ml) of the same polyfluoroacetal was obtained. Selectivity to this acetal was 97.9%.

In every case the remaining part of the reaction product was 3,3,3-trifluoropropanal.

EXAMPLE 14

The process of Example 9 was modified in that 250 g (5.43 mol) of ethanol was used in place of methanol. As the result 101.4 g (0.545 mol) of 1,1-diethoxy-3,3,3-trifluoropropane was obtained, and selectivity to this polyfluoroacetal was 92.2%. The remaining part of the reaction product was 3,3,3-trifluoropropanal.

EXAMPLE 15

The process of Example 14 was modified in that the quantity of ethanol was decreased to 125 g (2.72 mol) and that 125 g of 1,4-dioxane was additionally used. In this case 114.1 g (0.613 mol) of 1,1-diethoxy-3,3,3-trifluoropropane was obtained. Selectivity to this acetal was 98.0%, and the remaining part of the reaction product was 3,3,3-trifluoropropanal.

EXAMPLE 16

In a glass autoclave, a mixture of 150 g (4.69 mol) of methanol, 150 g of 1,4-dioxane, 3.0 g (0.017 mol) of PdCl$_2$, 5.8 g (0.034 mol) of CuCl$_2$.2H$_2$O and 4.0 g of Al(OH)$_3$ was kept heated at 60° C. Stirring the mixture, 3,3,3-trifluoropropene was continuously introduced into the autoclave so as to keep the gas pressure in the autoclave at 8 kg/cm$^2$. This operation was continued for 10 hr. As the result 245.2 g (1.552 mol) of 1,1-dimethoxy-3,3,3-trifluoropropane was obtained. In this case selectivity to this acetal was 60.2%, and the remaining part of the reaction product was 3,3,3-trifluoropropanal.

EXAMPLE 17

The process of Example 1 was modified only in that 125 g (2.02 mol) of ethylene glycol was used in place of methanol. As the result 87.8 g (0.556 mol) of 2-(2,2,2-trifluoroethyl)-1,3-dioxorane was obtained, and selectivity to this acetal was 91.5%.

When X in the general formula represents two —OR groups wherein R is an alkylene group as in the case of the compound formed in Example 17, the two —OR groups directly join to each other at the free ends of the respective alkylene groups so that the two —OR groups and the adjacent CH radical form a ring.

What is claimed is:

1. A method of preparing a polyfluoroaldehyde represented by the formula (1),

$$\text{RfCH}_2\text{CHO} \qquad (1)$$

wherein Rf represents a perfluoroalkyl group having not more than 12 carbon atoms, the method comprising the step of reacting a polyfluoroalkene represented by the formula (2):

$$\text{RfCH}=\text{CH}_2 \qquad (2)$$

wherein Rf is as defined above with respect to the formula (1), with water in the presence of a source of divalent palladium selected from the group consisting of palladium chloride, palladium sulfate, palladium nitrite, palladium acetate and metallic palladium, with the proviso that metallic palladium is used in combination with an oxidizer selected from the group consisting of copper salts, iron salts, heterophosphoric acid and p-benzoquinone.

2. A method according to claim 1, wherein said Rf represents a perfluoroalkyl group having not more than 3 carbon atoms.

3. A method according to claim 1, wherein said polyfluoroalkene is 3,3,3-trifluoropropene.

4. A method according to claim 1, wherein the source of divalent palladium is a palladium salt selected from the group consisting of palladium chloride, palladium sulfate, palladium nitrate and palladium acetate, and wherein the reaction is carried out in the presence of an oxidizer for oxidizing metallic palladium isolated by the reaction to divalent palladium.

5. A method according to claim 4, wherein said oxidizer is selected from the group consisting of copper salts, iron salts, heteropolyphosphoric acid and p-benzoquinone.

6. A method according to claim 5, wherein said oxidizer is cupric chloride.

7. A method according to claim 5, wherein the reaction is carried out in the presence of molecular oxygen.

8. A method according to claim 1, wherein said water is mixed with an organic solvent.

9. A method according to claim 8, wherein said organic solvent is selected from the group consisting of acetic acid, 1,4-dioxane and 3-methylsulfolane.

10. A method according to claim 8, wherein the mixture of water and said organic solvent contains 1–50 vol % of water.

11. A method according to claim 1, wherein the reaction is carried out in the presence of a fluorine removing agent.

12. A method according to claim 11, wherein said fluorine removing agent is aluminum hydroxide.

13. A method according to claim 1, wherein the reaction is carried out at a temperature in the range from about 50° C. to 90° C.

* * * * *